United States Patent
Hanley et al.

(10) Patent No.: US 9,951,018 B2
(45) Date of Patent: Apr. 24, 2018

(54) PROCESS FOR THE PREPARATION OF 4-ALKOXY-3-HYDROXYPICOLINIC ACIDS

(71) Applicant: Dow AgroSciences LLC, Indianapolis, IN (US)

(72) Inventors: Patrick S. Hanley, Midland, MI (US); Nakyen Choy, Carmel, IN (US); Thomas L. Siddall, Zionsville, IN (US); Gregory T. Whiteker, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/443,446

(22) Filed: Feb. 27, 2017

(65) Prior Publication Data
US 2017/0247330 A1    Aug. 31, 2017

Related U.S. Application Data

(60) Provisional application No. 62/301,107, filed on Feb. 29, 2016.

(51) Int. Cl.
*C07D 213/803* (2006.01)
*C07D 213/84* (2006.01)

(52) U.S. Cl.
CPC ....... *C07D 213/803* (2013.01); *C07D 213/84* (2013.01)

(58) Field of Classification Search
None
See application file for complete search history.

(56) References Cited

U.S. PATENT DOCUMENTS

| | | | |
|---|---|---|---|
| 9,475,771 B2 * | 10/2016 | Renga | C07D 213/84 |
| 9,481,651 B2 * | 11/2016 | Renga | C07D 213/84 |
| 9,522,887 B2 | 12/2016 | Renga | |
| 9,718,783 B2 * | 8/2017 | Renga | C07D 213/803 |

OTHER PUBLICATIONS

N. Cilauson-Kaas, J.B. Peterson, G.O. Sorensen, G. Jansen, Acta. Chem. Scand. 19 (1965) 1147.

* cited by examiner

*Primary Examiner* — Zinna Northington Davis
(74) *Attorney, Agent, or Firm* — Charles W. Arnett

(57) ABSTRACT

4-Alkoxy-3-hydroxypicolinic acids may be conveniently prepared from 2-hydroxypicolinonitrile in a series of chemical steps selected from chlorination, chloro substitution, nitrile hydrolysis and chloro reduction.

8 Claims, No Drawings

PROCESS FOR THE PREPARATION OF 4-ALKOXY-3-HYDROXYPICOLINIC ACIDS

FIELD

The present disclosure concerns a process for the preparation of 4-alkoxy-3-hydroxypicolinic acids. More particularly, the present disclosure concerns a process for the preparation of 4-alkoxy-3-hydroxypicolinic acids from furfural.

BACKGROUND

U.S. Pat. No. 6,521,622 B1 and U.S. application Ser. Nos. 61/747,723 and 14/142,183, the disclosures of which are hereby incorporated by reference in their entireties, describe inter alia certain heterocyclic aromatic amide compounds of general Formula

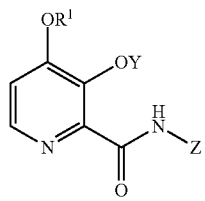

and their use as fungicides.

These disclosures also describe the preparation of 4-alkoxy-3-hydroxypicolinic acids as key intermediates in the preparation of these heterocyclic aromatic amide compounds. It would be useful to have an efficient and scalable process route to 4-alkoxy-3-hydroxypicolinic acids from inexpensive raw materials.

SUMMARY

The present disclosure concerns processes for the preparation of 4-alkoxy-3-hydroxypicolinic acids of Formula A

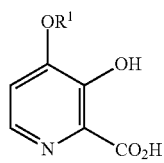

wherein $R^1$ is a $C_1$-$C_3$ alkyl;
from the compound of Formula B

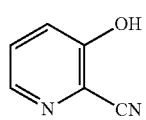

The compound of Formula A may be prepared in a multi-step process which comprises the following steps:
a) creating a first mixture by combining together the compound of Formula B and a chlorinating agent to form a first mixture;
b) isolating a compound of Formula C from the first mixture;

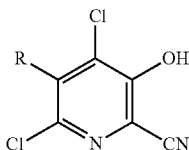

wherein R is H or Cl.
c) creating a second mixture containing an alkali metal alkoxide of Formula D $$MOR^1 \quad\quad D$$

wherein M is Na or K, and $R^1$ is a $C_1$-$C_3$ alkyl;
and the compound of Formula C;
e) isolating a compound of Formula E from the second mixture

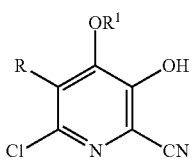

wherein R is H or Cl, and $R^1$ is a $C_1$-$C_3$ alkyl;
f) creating a third mixture containing the compound of Formula E, water, and one of a mineral acid and a strong base;
g) heating the third mixture;
h) isolating a compound of Formula F from the third mixture

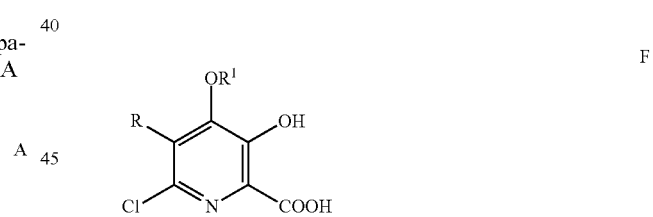

wherein R is H or Cl and $R^1$ is a $C_1$-$C_3$ alkyl;
i) creating a fourth mixture containing the compound of Formula F and a reducing agent; and
j) isolating the compound of Formula A from the fourth mixture.

The present disclosure also concerns a process for the preparation of the trichloro-3-hydroxypicolinonitrile of Formula C

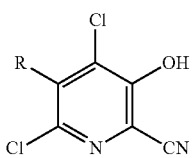

wherein R is Cl;

from the compound of Formula B

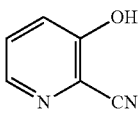

in a process which comprises the following steps:
a) creating a mixture by combining together the compound of Formula B and sulfuryl chloride to form a mixture;
b) heating the mixture; and
c) isolating the compound of Formula C from the heated mixture, wherein R is Cl.

Another aspect of the present disclosure are the novel intermediates produced in the present process, viz., compounds selected from the group consisting of:

a)

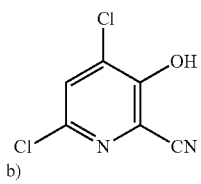

b)

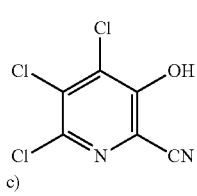

c)

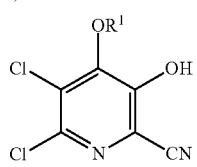

wherein $R^1$ is a $C_1$-$C_3$ alkyl;

d)

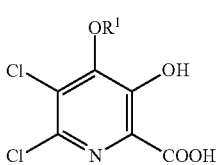

wherein $R^1$ is a $C_1$-$C_3$ alkyl;

e)

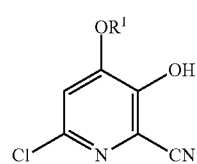

wherein $R^1$ is a $C_1$-$C_3$ alkyl;

f)

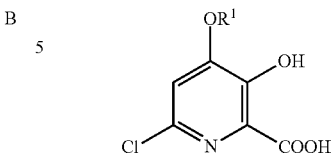

wherein $R^1$ is a $C_1$-$C_3$ alkyl;

DETAILED DESCRIPTION

The terms "isolate," "isolating," or "isolation" as used herein mean to partially or completely remove the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from ≤50% to ≥50%, and may be purified to a higher purity level using standard purification methods. The isolated product may also be used in a subsequent process step with or without purification.

In the processes described herein, 4-alkoxy-3-hydroxypicolinic acids of Formula A are prepared from 3-hydroxypicolinonitrile (B) in a series of chemical steps involving chlorination, substitution of a chloro group by an alkoxide group, nitrile hydrolysis, and halogen reduction. Some of the individual steps may be performed in different sequences of order. 3-Hydroxypicolinonitrile of Formula B is readily prepared from furfural as disclosed in U.S. application Ser. No. 14/794,430.

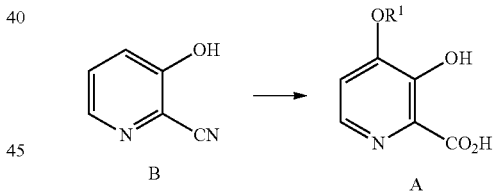

A. Preparation of the Compound of Formula C

In the process shown in Scheme I, chlorination of 3-hydroxypicolinonitrile B can furnish a mixture of mono-, di- and trichloro-3-hydroxypicolinonitriles depending upon the chlorination reagent used. Utilizing chlorine gas provides a low yield of a mixture of the di- and trichloropicolinonitriles C (R═H, Cl), whereas chlorination of B with 1,3-dichloro-5,5-dimethylhydantoin produces mainly the mono-chlorination product B1 and smaller amounts Scheme I

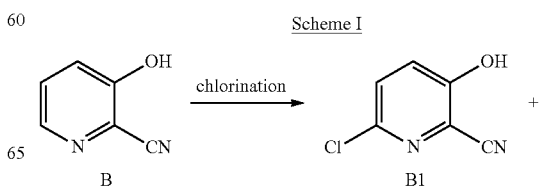

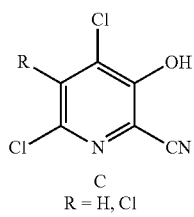

C
R = H, Cl of the di- and trichloropicolinonitriles C (R═H, Cl). Chlorination of B with sulfuryl chloride, however, provides predominantly the trichloropicolinonitrile of Formula C (R═Cl) in very good yield. Reaction solvents for the chlorination reaction can be selected from the group including water, acetonitrile, sulfolane, DMF, DMSO and mixtures thereof.

B. Preparation of the Compound of Formula A

The chemical steps used to convert compound C (R═H, Cl) into the 4-alkoxy-3-hydroxypicolinic acid of Formula A are shown in Scheme II. In the substitution reaction to replace the 4-chloro group of the compound of Formula C with an alkoxy group (Step a), use of an alkali metal alkoxide of formula $MOR^1$ (M is an alkali metal; $R^1$ is a $C_1$-$C_3$ alkyl) produces the 4-alkoxypicolinonitrile of Formula D (R═H, Cl). At least 2 equivalents, and preferably 2-5 equivalents, of the alkali metal alkoxide are used in this reaction. Typical alkali metal alkoxides useful in this reaction include sodium or potassium, methoxide, ethoxide, 1-propoxide or 2-propoxide. The reaction may be carried out in a protic solvent or reaction medium such as methanol (for methoxide), ethanol (for ethoxide), 1-propanol (for 1-propoxide) or 2-propanol (for 2-propoxide), or mixtures of methanol, ethanol, 1-propanol or 2-propanol with a polar, aprotic co-solvent such as DMSO, DMF, sulfolane or NMP. The reaction may also be conducted with an alkali metal alkoxide in one or more of the polar, aprotic solvents in the absence of an alcohol co-solvent. The temperature at which the reaction is conducted is between about 20° C. and about 150° C., preferably between about 40° C. and about 100° C. The substitution reaction generally requires from about 1 to about product is recovered by employing standard isolation and purification techniques.

In some embodiments, the preparation of the compound of Formula D (R═H, Cl) from the compound of Formula C may be conducted by employing solvent mixtures including at least one of a protic solvent and a polar aprotic solvent whereby the volume percent (vol %) ratio of the protic solvent to the polar aprotic solvent in the total solvent mixture ranges from about 100:0 to about 0:100. In some embodiments the volume percent (vol %) ratio of the protic solvent to the polar aprotic solvent in the total solvent mixture is 80-100 vol % protic solvent to 0-20 vol % polar aprotic solvent, 60-80 vol % protic solvent to 20-40 vol % polar aprotic solvent, 40-60 vol % protic solvent to 40-60 vol % polar aprotic solvent, 20-40 vol % protic solvent to 60-80 vol % polar aprotic solvent, or 0-20 vol % protic solvent to 80-100 vol % polar aprotic solvent. Preferable volume percent (vol %) ratios of the protic solvent to the polar aprotic solvent are from about 0.01-10 vol % protic solvent to about 90-99.99 vol % polar aprotic solvent. In some embodiments the solvent mixtures used to prepare the compound of Formula D ($R^1$═$CH_3$) from the compound of Formula C are methanol and DMSO, methanol and DMF, methanol and sulfolane, or methanol and NMP.

In the hydrolysis reaction of the nitrile group of the 4-alkoxy-3-hydroxypicolinonitriles of Formulas D and F to produce the 4-alkoxy-3-hydroxypicolinic acids of Formulas E and A, respectively (Steps b in Scheme II), the starting picolinonitriles are typically suspended in a strong, aqueous mineral acid reaction medium and heated for a period of time at elevated temperature with good mixing. Strong mineral acids useful in the hydrolysis reaction include sulfuric acid, phosphoric acid, hydrochloric acid and hydrobromic acid. Preferred, strong mineral acid reaction mediums include aqueous sulfuric acid mixtures such as about 25%, about 30%, about 35%, about 40%, about 45%, about 50%, about 55%, about 60%, about 65%, about 70%, about 75% or about 80% sulfuric acid in water on a weight basis. Most preferably, from about 25% to about 70% sulfuric acid in water may be used. The temperature at which the hydrolysis reaction may be conducted is usually between about Scheme II

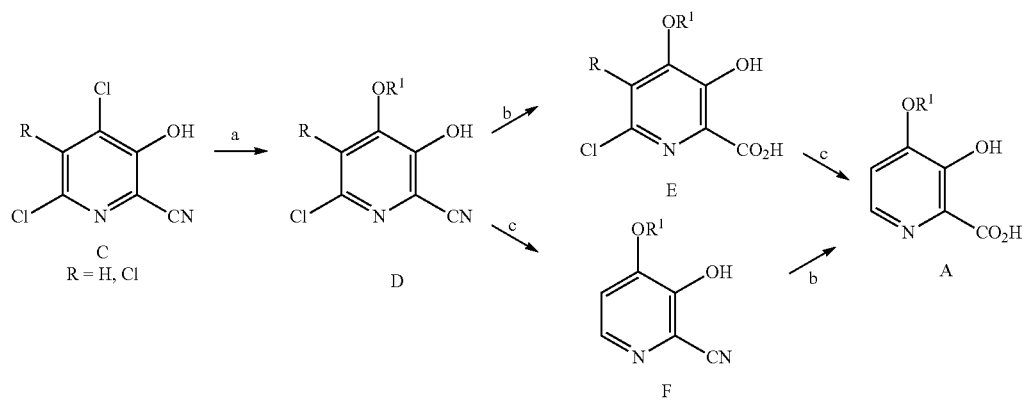

48 hours to proceed to completion and may be conducted under pressure in a sealed vessel to prevent the loss of volatile solvents. After the reaction is complete, the desired 75° C. and about 150° C. and preferably between about 80° C. and about 120° C. The hydrolysis reaction generally requires from about 8 to about 48 hours, preferably from about 8 to about 36 hours, to reach completion. After the reaction is complete, the desired product

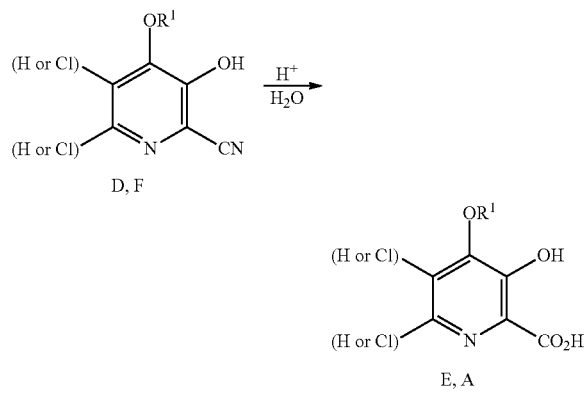

is recovered by cooling and slowly pouring the reaction mixture into cold water and employing standard isolation and purification techniques.

In some embodiments, the hydrolysis reaction of the nitrile group of the 4-alkoxy-3-hydroxypicolinonitriles of Formulas D and F to produce the 4-alkoxy-3-hydroxypicolinic acids of Formulas E and A, respectively (Steps b in Scheme II), the starting picolinonitriles are suspended in an aqueous reaction medium containing a strong base, such as an hydroxide of an alkali or alkaline earth metal, and heated for a period of time at elevated temperature with good mixing. Strong bases for use in the hydrolysis of the picolinonitriles include sodium hydroxide and potassium hydroxide. The concentration of the strong base used in the hydrolysis of the picolinonitriles may range from about 10 to about 40 weight percent (wt %), from about 15 to about 40 wt %, from about 20 to about 40 wt %, from about 30 to about 40 wt %, or from about 15 to about 25 wt %. The molar equivalent ratio of strong base to the nitrile starting material for the hydrolysis reaction may range from about 3:1 to about 10:1, preferably from about 4:1 to about 7:1. The temperature at which the strong base hydrolysis reaction may be conducted is usually between about 75° C. and about 150° C. and preferably between about 80° C. and about 120° C. The strong base hydrolysis reaction generally requires from about 8 to about 48 hours, preferably from about 8 to about 36 hours, to reach completion. After the hydrolysis reaction is complete, the desired product may be isolated by acidifying the reaction mixture and employing standard isolation and purification techniques.

Removal of the chloro groups from the 5- and 6-positions of the compound of Formula E to produce the reduced product of Formula A may be achieved by catalytic reduction using a hydrogen source and a transition metal catalyst.

In the catalytic reduction with hydrogen, suitable hydrogen sources include hydrogen gas or hydrogen transfer reagents such as ammonium, potassium or sodium formate. Suitable transition metal catalysts include, but are not limited to, palladium on carbon (Pd/C) and Raney nickel (Ra/Ni). These catalysts may be used at levels from about 0.01% to about 10% on a weight basis of the metal to the chloropyridine substrate. Exemplary solvents for use in this reaction include methanol, ethanol, isopropanol, ethyl acetate, and acetic acid. A soluble base such as, for example, triethylamine is normally used in the catalytic reduction with

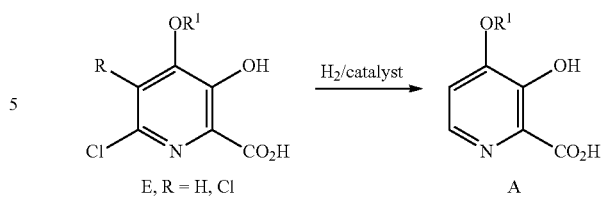

hydrogen. From about 2 to about 4 molar equivalents of the soluble base are normally used. When hydrogen gas is used as the hydrogen source, the reduction reaction may be conducted under an atmospheric pressure of hydrogen gas, or at elevated pressures of hydrogen gas such as 10, 20, 40, 60, 80, 100, 200, 300, 400, 500, 600, 700, 800, 900, 1000 pounds or more, per square inch (psi) above atmospheric pressure, or incremental hydrogen gas pressures between these values. After the catalytic reduction reaction is complete, the desired product is recovered by employing standard isolation and purification techniques.

In some embodiments, removal of the chloro groups from the 5- and 6-positions of the compound of Formula D to produce the reduced product of Formula F might be achieved by catalytic reduction using a hydrogen source and a transition metal catalyst.

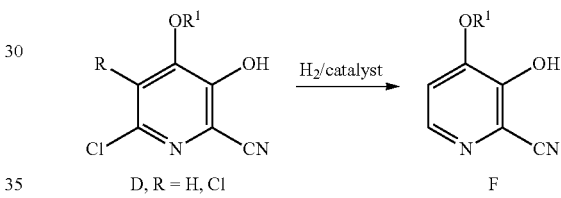

The products obtained by any of these processes, can be recovered by conventional means, such as evaporation, filtration or extraction, and can be purified by standard procedures, such as by recrystallization or chromatography.

The following examples are presented to illustrate the disclosure.

EXAMPLES

Example 1a. 4,6-Dichloro-3-hydroxypicolinitrile and 4,5,6-trichloro-3-hydroxypicolinitrile

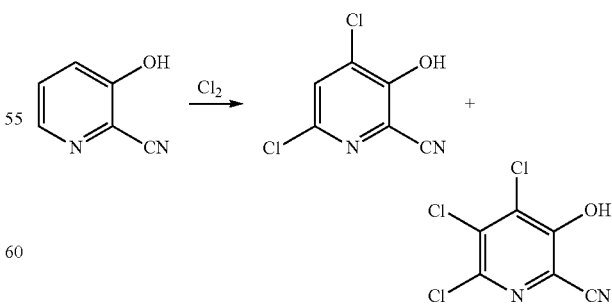

3-Hydroxypicolinitrile (2.4 g, 20 mmol) and sodium acetate (2.5 g, 30 mmol) were dissolved in acetonitrile (120 ml) and water (30 ml). The mixture was cooled to ⁻15 to ⁻20° C. and treated with a slow stream of chlorine until 1.7 g of chlorine had been dispensed. The mixture was warmed to −2 to −4° C., another 9.0 g of chlorine was dispensed into the mixture and stirring was continued for 90 minutes. The excess chlorine was destroyed by addition of sodium bisulfite solution and two phases were formed. The phases were separated and the aqueous phase was extracted with 100 mL of dichloromethane. The combined organic phases were washed with 20 mL of sat. NaCl solution, dried (Na$_2$SO$_4$) and evaporated under vacuum. The crude material was purified by RP-HPLC using a YMC-AQ column eluting with 50% aqueous acetonitrile containing 0.20% v/v H$_3$PO$_4$ to provide 550 mg of 4,6-dichloro-3-hyroxypicolinitrile and 660 mg of 4,5,6-trichloro-3-hydroxypicolinitrile as white solids which decomposed when heated for melting point determination. 4,6-Dichloro-3-hyroxypicolinitrile: $^1$H NMR (400 MHz, DMSO-d6) δ 8.08 (s, 1H). $^{13}$C NMR (101 MHz, DMSO-d6) δ 154.26, 140.14, 135.24, 129.48, 121.14, 114.58; ESIMS m/z 187 [(M-H)−]. 4,5,6-trichloro-3-hydroxypicolinitrile: $^{13}$C NMR (101 MHz, DMSO-d6) δ 155.16, 137.98, 134.29, 133.17, 118.63, 114.49. ESIMS m/z 221 [(M-H)−].

Example 1b. 6-Chloro-3-hyroxypicolinitrile, 4,6-dichloro-3-hyroxypicolinitrile and 4,5,6-trichloro-3-hydroxypicolinitrile

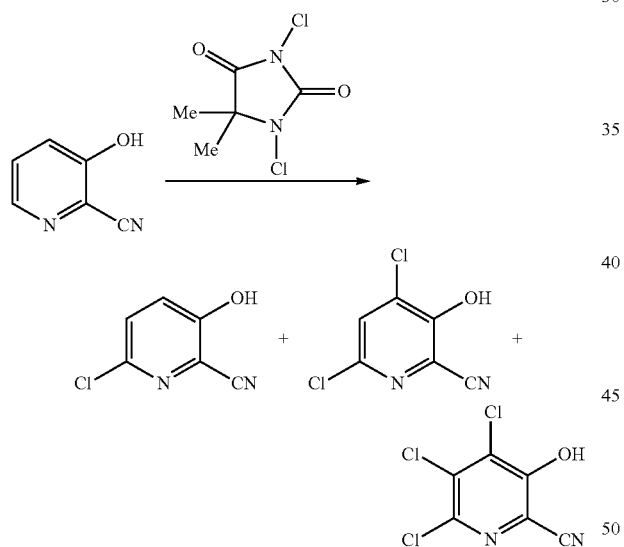

3-Hydroxypicolinonitrile (500 mg, 4.2 mmol) was combined with 1,3-dichloro-5,5-dimethylhydantoin (900 mg, 4.6 mmol) in 2.5 mL of dry acetonitrile and heated at 50° C. for 20 h. After cooling, the mixture was stirred with 30 mL of ethyl acetate and 10 mL of 20% sodium bisulfite solution. The organic phase was washed with 10 mL water and 10 mL of sat. NaCl solution, dried (Na$_2$SO$_4$) and evaporated. The residue was chromatographed by RP-HPLC using a YMC-AQ column eluting with 50% aqueous acetonitrile containing 0.20% v/v H$_3$PO$_4$ to provide 300 mg of 6-chloro-3-hydroxypicolinitrile, 84 mg of 4,6-dichlorohydroxypicolinitrile and 214 mg of 4,5,6-trichlorohydroxypicolinitrile.

Example 1c. 4,5,6-trichloro-3-hydroxypicolinitrile

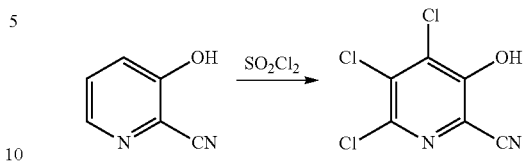

To a 3-necked 100 mL round bottom flask equipped with a thermoprobe and a condenser was added 3-hydroxypicolinonitrile (2.00 g; 1.67 mmol) and sulfolane (15 mL). The reaction mixture was heated to 62° C. and 4.2 mL of sulfuryl chloride was slowly added. After 3 h of stirring at 62° C., the reaction mixture was sampled and analyzed by LC-MS which showed about 75% formation of the desired trichlorinated product. To the mixture was added an additional 1.0 mL of sulfuryl chloride. The reaction mixture was stirred overnight at 62° C. after which LC-MS showed >90% conversion to the desired product. The reaction mixture was cooled to room temperature and water (25 mL) was added. The organics were extracted with ethyl acetate (150 mL), dried over MgSO$_4$, and the volatiles were removed by vacuum to reveal an orange oil. The crude product was purified by flash chromatography (hexane-ethyl acetate gradient) to provide 4,5,6-trichloro-3-hydroxypicolinonitrile as a yellow solid (2.30 g; 62%): $^{13}$C NMR (101 MHz, DMSO) δ 155.4, 137.7, 134.3, 133.1, 118.6. 114.6. HRMS ESI (m/z) [M]− for C$_6$HCl$_3$N$_2$O, 221.9154; measured, 220.9087.

Example 1d. 5,6-Dichloro-3-hydroxy-4-methoxypicolinonitrile

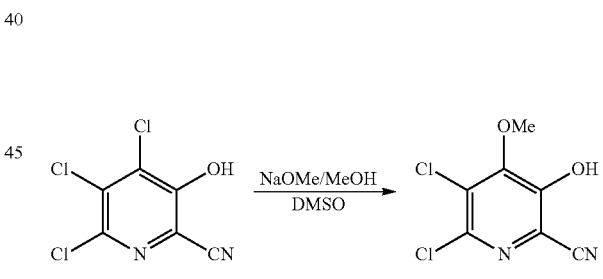

To a magnetically stirred solution of 4,5,6-trichloro-3-hydroxypicolinonitrile (867 mg, 3.88 mmol) in DMSO (8 mL) was added 30% sodium methoxide (3.494 g, 19.40 mmol) in MeOH solution at room temperature. The reaction mixture was heated at 50° C. for 2 h. The reaction mixture was cooled to 15-20° C. and quenched with 1.5N HCl. The aq layer (pH 1) was extracted twice with MTBE. The combined organic layers were concentrated and the concentrate purified by normal phase chromatography (CH$_2$Cl$_2$-MeOH) to give 5,6-dichloro-3-hydroxy-4-methoxypicolinonitrile (700 mg, 3.20 mmol, 82% yield) as an off-white solid. $^1$H NMR (400 MHz, DMSO-d6) δ 3.96 (s, 3H); $^{13}$C NMR (101 MHz, DMSO-d6) δ 154.55, 152.59, 139.02, 127.59, 118.53, 114.57, 61.31; HRMS-ESI (m/z) [M]+ calcd for C$_7$H$_4$Cl$_2$N$_2$O$_2$, 217.965; found, 217.9654.

Example 1e.
6-Chloro-3-hydroxy-4-methoxypicolinonitrile

To a magnetically stirred solution of 4,6-dichloro-3-hydroxypicolinonitrile (150 mg, 0.794 mmol) in DMSO (3 mL) was added 30% sodium methoxide (715 mg, 3.97 mmol) in MeOH solution at room temperature. The reaction mixture was heated at 50° C. for 18 h. The reaction mixture was cooled to 15-20° C. and quenched with 1.5N HCl. The aq layer (pH-1) was extracted twice with MTBE. The combined organic layers were concentrated and the concentrate purified by normal phase chromatography ($CH_2Cl_2$-MeOH) to give 6-chloro-3-hydroxy-4-methoxypicolinonitrile (110 mg, 0.596 mmol, 75% yield) as an off-white solid. $^1$H NMR (400 MHz, DMSO-d6) δ 11.61 (s, 1H), 7.40 (s, 1H), 3.98 (s, 3H); $^{13}$C NMR (101 MHz, DMSO-d6) δ 156.96, 148.97, 141.41, 117.68, 114.98, 111.22, 57.23; HRMS-ESI (m/z) [M]+ calcd for $C_7H_5ClN_2O_2$, 184.0041; found, 184.0040.

Example 1f.
5,6-Dichloro-3-hydroxy-4-methoxypicolinic acid

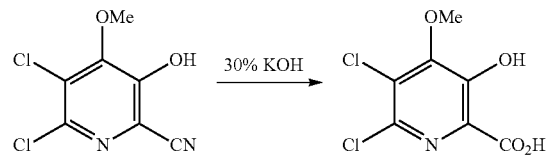 [SMILES: COc1c(O)c(C#N)nc(Cl)c1Cl ; COc1c(O)c(C(=O)O)nc(Cl)c1Cl]

Into the solid of 5,6-dichloro-3-hydroxy-4-methoxypicolinonitrile (153 mg, 0.7 mmol) was added 30% KOH (4 mL) at room temperature, and the mixture stirred overnight at 90-95° C. After the reaction was complete, the reaction mixture was cooled to rt and the pH adjusted to 2-3 with 3N HCl. The precipitated solid was collected, washed with water and dried to afford 5,6-dichloro-3-hydroxy-4-methoxypicolinic acid (165 mg, 0.693 mmol, 99% yield) as a white solid: $^1$H NMR (400 MHz, DMSO-d6) δ 4.03 (s, 3H); $^{13}$C NMR (101 MHz, DMSO-d6) δ 168.70, 154.37, 153.49, 134.62, 131.82, 124.09, 60.23; HRMS-ESI (m/z) [M]+ calcd for $C_7H_5Cl_2NO_4$, 236.9596; found, 236.9591.

Example 1g.
6-Chloro-3-hydroxy-4-methoxypicolinic acid

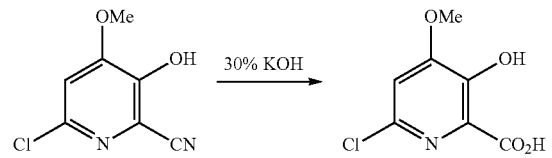 [SMILES: COc1cc(Cl)nc(C#N)c1O ; COc1cc(Cl)nc(C(=O)O)c1O]

A mixture of 6-chloro-3-hydroxy-4-methoxypicolinonitrile (80 mg, 0.433 mmol) in 30% KOH (5 mL) was stirred at 90° C. for 20 h. The reaction mixture was cooled to room temperature, followed by adding 6N HCl slowly to precipitate the product. The solid was filtered and washed with water to give 6-chloro-3-hydroxy-4-methoxypicolinic acid (60 mg, 0.295 mmol, 68.0% yield) as a white solid: $^1$H NMR (400 MHz, DMSO-d6) δ 7.29 (s, 1H), 3.92 (s, 3H); $^{13}$C NMR (101 MHz, DMSO-d6) δ 170.16, 156.99, 148.72, 139.90, 129.31, 111.03, 56.80; HRMS-ESI (m/z) [M]+ calcd for $C_7H_6ClNO_4$, 202.9985; found, 202.9990.

Example 1i. 3-Hydroxy-4-methoxypicolinic acid

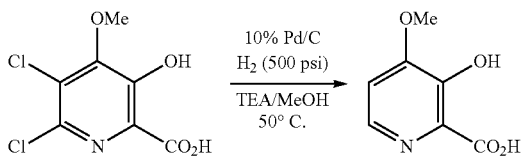 [SMILES: COc1c(O)c(C(=O)O)nc(Cl)c1Cl ; COc1ccnc(C(=O)O)c1O]

To 3-hydroxy-6-bromo-4-methoxypicolinic acid (60 mg) and MeOH (5 mL) in a pressure tube (50 mL) was added triethylamine (51 mg). Then, under a nitrogen atmosphere, 10% Pd/C (20 mg) was added to the tube. The reaction slurry was placed under hydrogen gas (500 psi) and stirred at 50° C. After 20 hrs, the hydrogen gas was removed. The reaction slurry was filtered through a pad of celite and the celite pad was washed with fresh methanol. The methanolic filtrate was concentrated to give a solid. The solid was diluted with 0.2N HCl (10 mL) to adjust the pH to about 1-2 and the resulting suspension was collected by filtration, washed with water and dried in air for several hours and then in a vacuum oven at 50° C. to give 3-hydroxy-4-methoxypicolinic acid (20 mg) as a white solid in 45% yield: $^1$H NMR (400 MHz, DMSO-d6) δ 8.04 (d, J=6.4 Hz, 1H), 7.39 (d, J=6.5 Hz, 1H), 4.04 (s, 3H); $^{13}$C NMR (101 MHz, DMSO-d6) δ 164.16, 162.03, 152.52, 132.32, 126.57, 109.13, 57.35; HRMS-ESI (m/z) calcd for $C_7H_7NO_4$, 169.0379; found, 169.0375.

What is claimed is:
1. A process for the preparation of the compound of Formula A

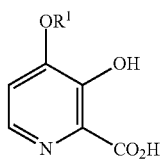

wherein $R^1$ is a $C_1$-$C_3$ alkyl;
from the compound of Formula B

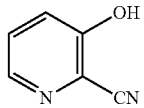

which comprises the following steps:
a) creating a first mixture by combining together the compound of Formula B and a chlorinating agent;
b) isolating a compound of Formula C from the first mixture;

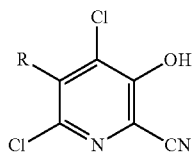

C wherein R is H or Cl;
c) creating a second mixture containing an alkali metal alkoxide of Formula D

MOR¹     D wherein M is Na or K, and $R^1$ is a $C_1$-$C_3$ alkyl;
and the compound of Formula C;
d) isolating a compound of Formula E from the second mixture

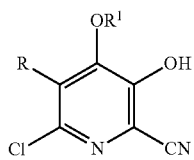

E wherein R is H or Cl and $R^1$ is a $C_1$-$C_3$ alkyl;
e) creating a third mixture containing the compound of Formula E, water, and one of a mineral acid and a strong base;
f) heating the third mixture;
g) isolating a compound of Formula F from the third mixture

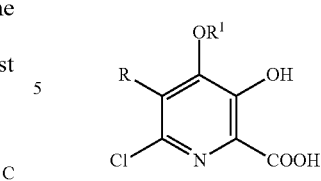

F wherein R is H or Cl and $R^1$ is a $C_1$-$C_3$ alkyl;
h) creating a fourth mixture containing the compound of Formula F and a reducing agent; and
i) isolating the compound of Formula A from the fifth mixture;

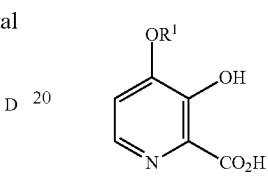

A wherein $R^1$ is a $C_1$-$C_3$ alkyl.

2. The process of claim 1 wherein the solvent for the first mixture is selected from the group including water, acetonitrile, sulfolane, DMSO and xylene.

3. The process of claim 1 wherein the chlorinating agent is selected from the group including chlorine, sulfuryl chloride and 1,3-dichloro-5,5-dimethylhydantoin.

4. The process of claim 1 wherein $R^1$ is $CH_3$.

5. The process of claim 1 wherein the mineral acid is sulfuric acid.

6. The process of claim 1 wherein the strong base is sodium hydroxide or potassium hydroxide.

7. The process of claim 1 wherein the reducing agent is comprised of hydrogen and a transition metal catalyst.

8. The process of claim 7 wherein the hydrogen is hydrogen gas and the transition metal catalyst is comprised of palladium on carbon.

* * * * *